United States Patent
Pompilio et al.

(10) Patent No.: US 10,791,961 B2
(45) Date of Patent: Oct. 6, 2020

(54) SYSTEM AND METHOD FOR MEASURING THE MECHANICAL IMPEDANCE OF THE RESPIRATORY SYSTEM

(75) Inventors: Pasquale Pio Pompilio, Milan (IT); Alessandro Gobbi, Turano Lodigiano (IT); Raffaele Dellaca', Como (IT); Antonio Pedotti, Milan (IT)

(73) Assignee: RESTECH S.R.L., Milan (MI) (IT)

( * ) Notice: Subject to any disclaimer, the term of this patent is extended or adjusted under 35 U.S.C. 154(b) by 669 days.

(21) Appl. No.: 13/812,180

(22) PCT Filed: May 17, 2011

(86) PCT No.: PCT/IB2011/001070
§ 371 (c)(1),
(2), (4) Date: Jan. 25, 2013

(87) PCT Pub. No.: WO2012/014024
PCT Pub. Date: Feb. 2, 2012

(65) Prior Publication Data
US 2013/0150747 A1  Jun. 13, 2013

(30) Foreign Application Priority Data
Jul. 26, 2010 (IT) .............................. BG2010A0042

(51) Int. Cl.
*A61B 5/085* (2006.01)
*A61M 16/00* (2006.01)
*A61B 5/087* (2006.01)

(52) U.S. Cl.
CPC ......... *A61B 5/085* (2013.01); *A61M 16/0006* (2014.02); *A61B 5/087* (2013.01); *A61M 2016/0027* (2013.01); *A61M 2016/0036* (2013.01); *A61M 2230/46* (2013.01)

(58) Field of Classification Search
CPC .......... A61B 5/08; A61B 5/085; A61B 5/091; A61B 5/097; A61B 5/093
USPC ................................ 600/529, 533, 538–543
See application file for complete search history.

(56) References Cited

U.S. PATENT DOCUMENTS

| | | |
|---|---|---|
| 3,713,436 A | 1/1973 | Hardway |
| 4,220,161 A * | 9/1980 | Berlin et al. ................... 600/533 |
| 4,333,476 A | 6/1982 | Downing, Jr. |
| 6,066,101 A | 5/2000 | Johnson et al. |

(Continued)

FOREIGN PATENT DOCUMENTS

| | | |
|---|---|---|
| EP | 1551293 B1 | 1/2009 |
| WO | 2010070498 A1 | 6/2010 |

*Primary Examiner* — Etsub D Berhanu
*Assistant Examiner* — Michael A Catina
(74) *Attorney, Agent, or Firm* — King & Schickli, PLLC

(57) ABSTRACT

A system for measuring the mechanical impedance of a patient's respiratory system during spontaneous respiratory activity, characterised by comprising a fan; a motor which operates said fan; said motor and said fan being positioned within a cavity; said cavity comprising an initial end and a final end, both providing access to the outside; said cavity presenting an impedance between said initial and said final end of less than 1 cm $H_2O/L/s$; said fan withdrawing air from said final end and providing pressure variations of small amplitude and of frequency >2 Hz to said initial end; said initial end comprising air pressure and air flow measurement means and a connection directly connected to the airway opening.

15 Claims, 2 Drawing Sheets

(56) References Cited

U.S. PATENT DOCUMENTS

| | | | |
|---|---|---|---|
| 6,142,952 A * | 11/2000 | Behbehani et al. | 600/533 |
| 6,257,234 B1 | 7/2001 | Sun | |
| 6,363,933 B1 | 4/2002 | Berthon-Jones | |
| 7,282,032 B2 * | 10/2007 | Miller | 600/538 |
| 7,325,545 B2 * | 2/2008 | Dellaca' et al. | 128/204.23 |
| 7,475,685 B2 * | 1/2009 | Dietz et al. | 128/204.23 |
| 2004/0249300 A1 | 12/2004 | Miller | |
| 2006/0100537 A1 * | 5/2006 | Williams et al. | 600/538 |
| 2006/0249150 A1 | 11/2006 | Dietz et al. | |
| 2008/0251075 A1 * | 10/2008 | Scarberry et al. | 128/204.18 |
| 2010/0147305 A1 * | 6/2010 | Dellaca' | A61B 5/085 128/204.23 |
| 2010/0275921 A1 * | 11/2010 | Schindhelm | A61B 5/08 128/204.23 |
| 2011/0232643 A1 * | 9/2011 | Mechlenburg et al. | 128/204.23 |
| 2012/0216812 A1 * | 8/2012 | Pastoor | A61M 16/0683 128/205.25 |
| 2013/0172772 A1 * | 7/2013 | Alshaer | A61B 5/087 600/538 |

\* cited by examiner

SYSTEM AND METHOD FOR MEASURING THE MECHANICAL IMPEDANCE OF THE RESPIRATORY SYSTEM

The present invention relates to a system and method for measuring the mechanical impedance of the respiratory system during spontaneous respiratory activity of the patient, without requiring the cooperation thereof, by using the forced oscillation technique (FOT or oscillometry). The invention enables compact portable devices to be formed, reducing to a minimum the dead space and the load added to the patient's airways.

The forced oscillation technique is a method for measuring the mechanical properties of the lung and airways based on an analysis of their response to small sinusoidal pressure stimuli generated externally. Although these techniques were introduced in 1956 (Journal of Applied Physiology—May 1956 vol. 8 no. 6 587-594), for many years they aroused little clinical interest because of the technical difficulties related to their implementation. Recently, because of technological progress in the digital electronic and calculator field, the use of oscillometric techniques for measuring the mechanical and functional properties of the respiratory system has generated increasing clinical interest as a potential new diagnosis and monitoring instrument.

In oscillometry, the mechanical characteristics of the respiratory system are measured by subjecting the respiratory system to an external small-amplitude mechanical stimulus and deriving its mechanical impedance (Z) defined as the complex ratio between the pressure ($P_{ao}$) and flow ($\dot{V}_{ao}$) measured at the inlet to the airways at a stimulus frequency:

$$Z(f) = \frac{P_{ao}(f)}{\dot{V}_{ao}(f)} = R(f) + jX(f)$$

The mechanical impedance is a complex number the real part of which, called the resistance (R(f)), synthesizes the dissipative properties of the system, while the imaginary part, called the reactance (X(f)), synthesizes the capacity of the system to store energy and is hence determined jointly by the elastic and inertial properties of the system.

Between its introduction and the present day, various measurement set-ups have been described and used. In its initial implementations, the system was composed of a stimulus generator consisting of a cylinder coupled to a piston the exit of which was directly connected to the airway opening (nose or mouth) and by a set of sensors for measuring flow and pressure (Journal of Applied Physiology—May 1956 vol. 8 no. 6 587-594, U.S. Pat. No. 3,713,436—Filed Oct. 23, 1970). Although this technology enabled complex stimulation waves to be generated with an optimal signal/noise ratio, it was not applicable during spontaneous respiration but only during apnea periods with the subject totally relaxed.

Subsequently, to enable this technique to be applied to measurements during spontaneous respiration, a new set-up was developed composed of an oscillation-generating loudspeaker, a respiratory circuit composed of a high inertance tube, necessary to permit spontaneous patient respiration and prevent stimulus dispersion into the external environment, and a set of pressure and flow sensors (The Journal of Clinical Investigation—November 1975 vol. 56 1210-1230, U.S. Pat. No. 4,333,476, EP 1 551 293). However by considerably increasing the dead space of the respiratory system, the presence of the high inertance tube requires the use of an additional flow generator for air refreshment, so increasing the dimensions and complexity of the overall system.

Reduced-dimension set-ups have been produced using actuators to partially or totally occlude the airways during spontaneous respiration such as to cause pressure disturbances within the circuit, where the stimulation energy is generated by the respiratory muscles, as described in U.S. Pat. Nos. 4,220,161 and 6,066,101.

Although the devices pertaining to this latter category are more economical and less bulky, they do not function for low exhaled and inhaled flows (e.g. at the end of inhalation and at the end of exhalation). This makes them unsuitable for measuring the respiratory mechanical variations which occur during the entire respiratory cycle.

Therapeutic ventilation systems are likewise known able to derive the respiratory impedance by the FOT technique as described in U.S. Pat. Nos. 6,257,234, 6,363,933 and WO 2010/070498.

As these combine the simultaneous generation of the low amplitude sinusoidal wave necessary for stimulating the system and making the measurement, with the auxiliary ventilation pressure wave, these systems must be able to generate high pressures (10-20 $cmH_2O$). For this purpose they use a pressure generator combined with one or more electronically controlled regulator valves. Consequently the complexity and the energy required for these systems make their dimensions such as to require the use of one or two tubes for connecting the patient's airway openings. In the case of a single tube, to prevent accumulation of exhaled $CO_2$, the pressure within it must be maintained greater than at least 3 $cmH_2O$ such as to generate a continuous refreshing flow through a discharge port provided in proximity to the patient. However this pressure, inhaled by the patient, prevents the making of impedance measurements at normal respiratory volumes.

An object of the present invention is to provide a system and method for measuring the mechanical impedance of the respiratory system, and in particular a system and method for generating small-amplitude pressure stimuli of predetermined form, for recording the air flow and pressure measurements, and for the numerical processing required to derive the mechanical impedance of the respiratory system, which is compact and usable for making measurements during spontaneous respiratory activity of the patient.

These and other objects are attained, according to the present invention, by a system for measuring the mechanical impedance of a patient's respiratory system during spontaneous respiratory activity, characterised by comprising a fan; a motor which operates said fan; said motor and said fan being positioned within a cavity; said cavity comprising an initial end and a final end, both providing access to the outside; said cavity presenting an impedance between said initial and said final end of less than 1 cm $H_2O$/L/s; said fan withdrawing air from said final end and providing pressure variations to said initial end; said initial end comprising air pressure and air flow measurement means and a connection directly connected to the airway opening.

The object is also attained by a method for measuring the mechanical impedance of the respiratory system, comprising the step of recording the air pressure and air flow measurements; said recording step comprising the stages of varying the rotational speed of a fan positioned within a cavity such as to force an air flow into said cavity to generate, in proximity to the airway opening, pressure oscillations of maximum amplitude less than or equal to 3-5 $cmH_2O$;

measuring the air pressure and air flow within said cavity in proximity to the subject's airways.

Further characteristics of the invention are described in the dependent claims.

Compared with similar technologies the present solution has the following advantages.

1. As the system has to generate pressure stimuli of small amplitude (peak-peak≤3 cmH$_2$O), a fan can be used as actuator in place of the blowers used by previous systems. As a result, the patient is able to breathe through it with minimum force without the need for additional alternative paths, the energy consumption hence being reduced to enable the motor dimensions to be reduced, and hence produce a portable system.

2. As the system composed in this manner is compact and of small dimensions, it is applied to the patient via a nozzle directly connected to the patient. As a result, the dead space of the system is extremely small, it hence not being necessary to pressurize the circuit in order to generate a continuous refreshing flow, so enabling measurement at pressures close to atmospheric. As a consequence, the patient is not insufflated and the impedance measurement is made at pulmonary volumes at which the patient normally breathes, hence being more representative of the normal operating conditions of the respiratory system.

3. It can be used to measure the mechanical impedance of the respiratory system during the patient's entire respiratory cycle.

4. It does not require respiratory manoeuvres to be carried out.

5. It can be used to measure intra-respiratory impedance variations. The system proposed herein consists of a cavity containing a rotary motor connected to a fan (axial or centrifugal) housed within the pneumatic circuit through which the patient breathes. The system includes a nozzle directly connected to the cavity and preferably designed such as to support the cheeks during the measurement, to reduce the shunt effects of the upper airways on the impedance measurement.

One or preferably more pressure and flow sensors are positioned within the circuit, preferably in proximity to the opening of the patient's airways. The pressure signals ($P_{ao}$) and flow signals ($\dot{V}_{ao}$) measured directly or indirectly at the airway opening are digitized and recorded preferably using an electronic system based on a microprocessor (µP) and used for calculating the inlet impedance of the respiratory system and of its variations during spontaneous respiration. Preferably these algorithms verify the correct signal-noise ratio during the measurement and, if necessary, act on the motor by accelerating and decelerating its rotational velocity such as to vary the amplitude and form of the pressure stimulus in proximity to the patient's airway opening in order to improve measurement quality.

The characteristics and advantages of the present invention will be evident from the ensuing description of a possible embodiment thereof, illustrated by way of non-limiting example in the accompanying drawings, in which.

Figure 1:
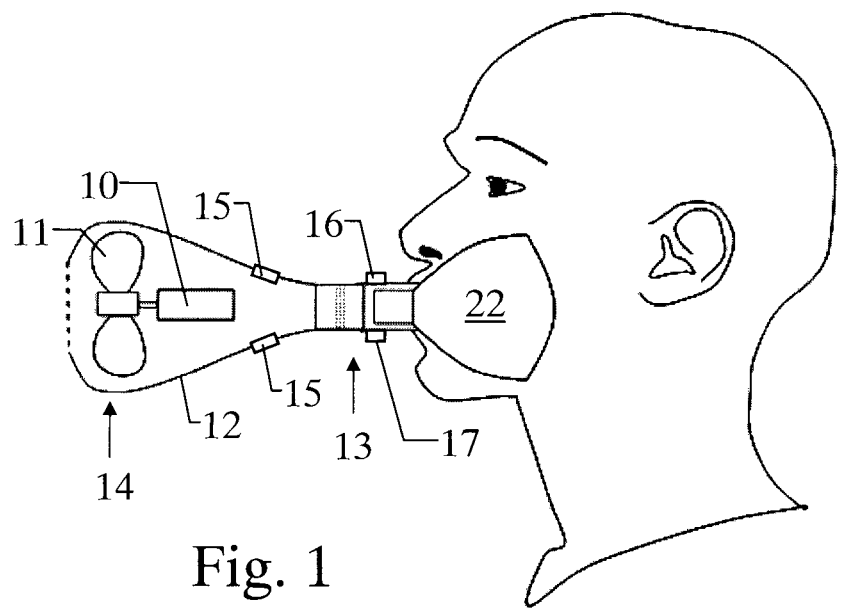
FIG. 1 shows a schematic representation of a system for measuring the mechanical impedance of the respiratory system applied to a patient, in accordance with the present invention.
Figure 2:
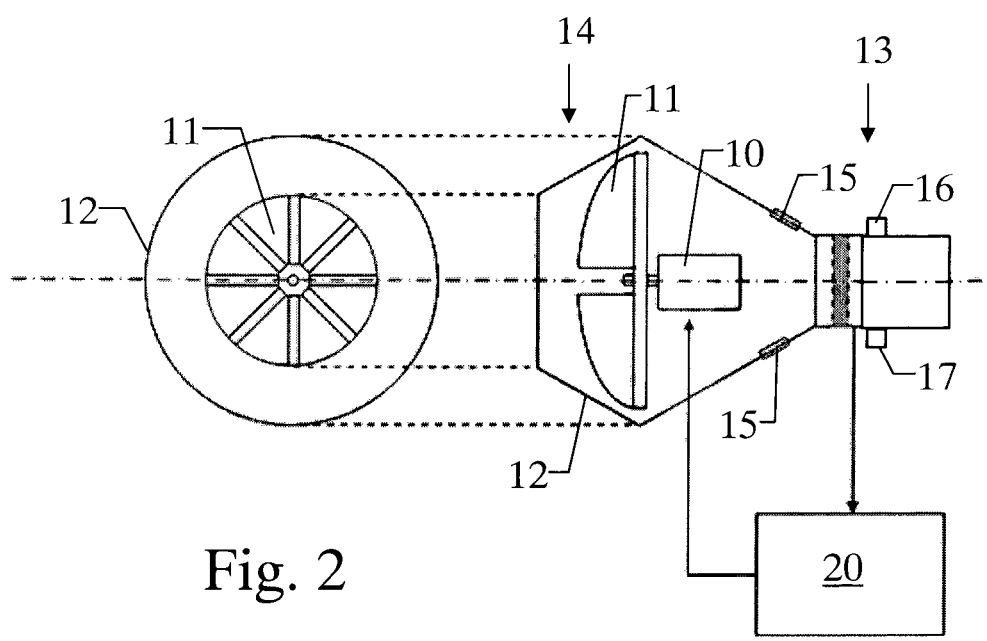
FIG. 2 shows a schematic representation of just the system for measuring the mechanical impedance of the respiratory system, in accordance with the present invention.
Figure 3:
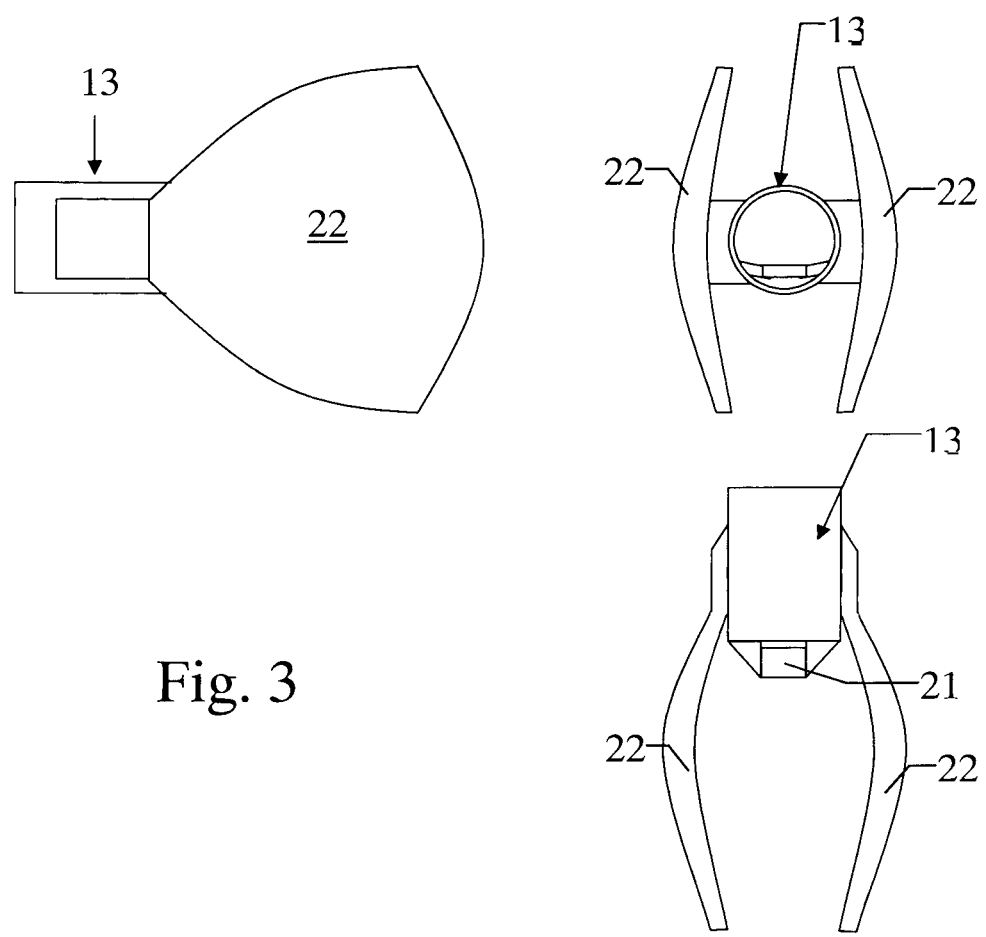
FIG. 3 shows a schematic representation of the nozzle for supporting the cheeks while measuring the mechanical impedance of the respiratory system, seen from three sides, in accordance with the present invention.

With reference to the accompanying figures, a system for measuring the mechanical impedance of the respiratory system, in accordance with the present invention, comprises a motor 10 connected to an axial fan 11.

The motor 10 and fan 11 are positioned in a cavity 12 (hydraulic circuit) substantially of conical form, having an initial end 13 and a final end 14, both with openings towards the outside.

The initial end 13 is arranged to be connected to a nozzle 21 or other interface with the patient and hence has a diameter of about 2-4 cm. The final end 14 has a greater diameter than the initial end 13, and equal to about 5-15 cm, as it has to contain the fan 11. After overcoming the enlargement for containing the fan 11, the cavity 12 has a diameter reduction to arrive at a diameter of about 4-5 cm, which determines the external opening of the cavity 12.

In an alternative embodiment, the cavity 12 can have a more simply cylindrical form open at its two bases, and a nozzle 21 applied to one of its bases.

in both cases, the length of the cavity 12 is less than 25 cm, the nozzle 21 having a length of about 5 cm. Hence from the rear air withdrawal end to the patient's airway opening the distance is very small and equal to or less than 30 cm.

If the volume of the cavity 12 is greater than 50 mL it preferably comprises one or more vent holes 15 positioned at about one half the distance between the initial end 13 and the final end 14, necessary to ensure outward diffusion of the exhaled air.

In one possible embodiment, the cavity 12 also comprises a pressure sensor ($P_{ao}$) 16 and a flow sensor ($\dot{V}_{ao}$) 17, positioned in strict proximity to the initial end 13. In another embodiment, the cavity 12 comprises only a pressure sensor ($P_{ao}$) 16 positioned in strict proximity to the initial end 13, and uses the electrical absorption values of the motor and/or its rotational velocity to indirectly measure the flow within said cavity.

Associated with the cavity 12 there is a microprocessor processing and control system 20 powered by the mains or batteries, which receives the signals from the sensors 16 and 17 and stores them in its memory, and implements the processing required to calculate the mechanical impedance of the respiratory system. It also comprises the control circuit for the motor 10, and a port for the external connection of the system 20 and for withdrawing the measurements made.

According to one embodiment, the processing and control device 20 for handling the measurements made comprises only a memory and electronic interfaces for withdrawing the data. In another embodiment it comprises not only the memory but also a data processing system to hence directly provide already processed data. In another embodiment, the device includes a system for transmitting wireless data.

In another embodiment, the device includes a system for transmitting data via the internet to external processing and storage systems.

The motor 10 can be for example of brushed type, the rotational velocity of which is controlled for example by using a current signal modulated by PWM (pulse-width modulation).

This technique enables the motor velocity to be controlled by modulating the duty cycle of an oscillating square wave.

Preferably, the duty cycle value is controlled by the control system 20 by a closed loop PID control algorithm using the pressure measurement (sensor 16) in proximity to the airway opening as the input variable.

The rotational velocity of the motor 10 is varied such as to force external air into the cavity 12 to produce, in proximity to the airway opening, and hence at the nozzle 21, pressure variations of a maximum amplitude equal to about 3 cmH$_2$O peak-peak, of predefined form, typically sinusoidal or the sum of sinusoids of frequency >2 Hz, typically between 5 and 20 Hz, and with a mean pressure value less than or equal to 1.5 cmH$_2$O.

In a preferred embodiment the mean pressure value is between 0.75 and 1 cmH$_2$O, hence the peak-peak pressure is between 1.5 and 2 cmH$_2$O.

To enable the patient to breathe spontaneously through the circuit with minimum force, the cavity containing the motor-fan unit is designed such as to have a maximum impedance equal to 1 cmH$_2$O/L/s, measured at normal breathing frequencies and hence within the range 0-1 Hz.

As the pressure increments required to make the measurement are of small amplitude 3 cmH$_2$O peak-peak), this requirement can be satisfied by using an axial fan having a total blade area and inclination such as to cause a flow resistance of less than 1 cmH$_2$O/L/s (given that the resistance of the cavity alone is negligible), or an in-line centrifugal fan having a total area not exceeding ¾ of the area of the cavity cross-section.

The measurement of the inlet impedance of the respiratory system made at the airway opening is affected by the presence of a shunt path formed by the upper airways (J Appl Physiol 1989; 66: 2274-2279). To reduce this effect, the patient or doctor is required to support the cheeks with the hands. To enable it to be also used in the absence of supervision, the system of the present invention uses a cheek-support nozzle specifically designed to reduce the cheek movement and hence the relative negative effects on the measurement result.

Laterally to the nozzle 21, which is located at the initial end 13 of the cavity 12, there are two plates 22 of slightly concave substantially triangular shape which, with the nozzle 21 in the mouth, are positioned on the patient's cheeks to exert a slight pressure (intrinsic of the plates) and hold them still.

The use of the system for measuring the mechanical impedance of the respiratory system here described is very simple. The apparatus (the control system 20) is switched on. The patient rests the nozzle 21 in the mouth and takes a series of breaths. In the meantime, the control system 20 operates the motor 10 as programmed, and the oscillatory mechanical and breathing pattern parameters are calculated using the pressure and flow values which, according to the present embodiment, are measured by the sensors 16 and 17.

The memorized and calculated values can be downloaded if required.

The impedance of the respiratory system can be calculated using an algorithm based on minimum square optimization reported by Horowitz (Comput Biomed Res 1983 December; 16(6):499-521.) and Kackza (Ann Biomed Eng 1999 May; 27(3):340-55) and recently improved by Dellaca et al. (EP1551293). This algorithm is based on decomposing the pressure and flow signals into those components due to normal respiratory activity and those due to external stimulation. These latter are then decomposed into their constitutive harmonics and to each of these an iterative calculation procedure is applied to identify the phasorial coefficients of each of them.

The calculation proceeds in parallel on the pressure and flow signals iteratively: at each iteration a time window of N samples centred on the sample k is processed. Inside each window the filtered signals can be considered as composed of a sinusoidal wave and a residual noise:

$$S(t) = r(t) + a_0 + a\cos(2\pi ft) - b\mathrm{sen}(2\pi ft) = r(t) + a_0 + \mathrm{Real}[(a+jb)e^{j2\pi ft}]$$

As the signals were digitized, the same equation can be rewritten in the following matrix form: $S = A \cdot X + R$
with $$A = \begin{bmatrix} 1 & \cos(\omega t_1) & -\mathrm{sen}(\omega t_1) \\ 1 & \cos(\omega t_2) & -\mathrm{sen}(\omega t_2) \\ \ldots & \ldots & \ldots \\ 1 & \cos(\omega t_N) & -\mathrm{sen}(\omega t_N) \end{bmatrix}$$

$$X = \begin{bmatrix} a_0(l) \\ a(l) \\ b(l) \end{bmatrix}$$

$$S = \begin{bmatrix} P(k) \\ P(k+1) \\ \ldots \\ P(k+N-1) \end{bmatrix}$$

where
ω=stimulus pulsation
k=iteration index
N=length of time window
l=k+window/2 if N is even, or k+(N−1)/2 if N is odd.

Resolving this system, the following expression is obtained for the signal phasorial coefficient matrix:

$$X = (A^T A)^{-1} A^T S$$

The matrix A and hence also the matrix $(A^T A)^{-1} A^T$ depend only on the stimulus frequency and therefore remain unvaried during the execution of the entire calculation.

Applying said equation to windows of pressure and flow data, the following respective factorial coefficients are obtained:

$$X_P(l) = (A^T A)^{-1} A^T S_P(l) = \begin{bmatrix} a_{0,P}(l) \\ a_P(l) \\ b_P(l) \end{bmatrix}$$

$$X_{\dot{V}}(l) = (A^T A)^{-1} A^T S_{\dot{V}}(l) = \begin{bmatrix} a_{0,\dot{V}}(l) \\ a_{\dot{V}}(l) \\ b_{\dot{V}}(l) \end{bmatrix}$$

From factorial coefficients for the pressure and flow signals, the following expression is obtained:

$$Zrs(l) = \frac{P}{\dot{V}} = \frac{a_P(l) + jb_P(l)}{a_{\dot{V}}(l) + jb_{\dot{V}}(l)}$$

For calculation purposes the window is shifted forwards by one sample and the aforedescribed procedure is reiterated.

This calculation is carried out for each of the harmonic components with which the stimulus signal is formed. The final result is composed of a number of impedance traces equal to double the signal component frequencies which vary with time.

In practice, the materials used and the for the system for measuring the mechanical impedance of the respiratory system, and the dimensions, can be chosen at will according to requirements and to the state of the art.

The invention claimed is:

1. A portable system for self-assessment of the mechanical impedance of a patient's respiratory system during a spontaneous breath, comprising a fan; a motor which operates said fan; said motor and said fan being positioned within a cavity and a speed of the fan controlling a pressure within the cavity; said cavity comprising an initial end and a final end, both providing access to an outside of the cavity; said cavity having a length between said initial end and said final end equal to or less than 25 cm; said cavity, including said motor and said fan, comprising an impedance between said initial end and said final end of less than 1 cm $H_2O/L/s$, measured at normal breathing frequencies within the range of 0-1 Hz; said fan having a total area not exceeding three-fourths of the area of a cross-section of the cavity; said fan withdrawing air from said final end and providing pressure variations, with maximum peak-peak amplitude equal to or less than 3 $cmH_2O$ and frequency greater than 2 Hz, to said initial end; said initial end comprising an air pressure and an air flow measurement means and a connection configured to be directly connected to an airway opening of the patient including means for reducing the motion of the patient's cheeks, wherein the distance between said final end and the patient's airway opening is configured to be less than 30 cm.

2. The system as claimed in claim 1, characterised in that the fan is controlled to generate in proximity to the patient's airway opening a variable pressure with a mean value less than 1.5 $cmH_2O$.

3. The system as claimed in claim 1, characterised in that said system comprises a memory for storing values measured by said measurement means.

4. The system as claimed in claim 1, characterised in that said system comprises a microprocessor processing and control system for processing necessary for obtaining the mechanical impedance of the respiratory system.

5. The system as claimed in claim 1, characterised in that said cavity comprises one or more holes positioned between said initial end and said final end.

6. The system as claimed in claim 1, characterised in that said motor is controlled to provide a variable air flow such as to generate, inside the cavity, pressure values which follow a predetermined pattern.

7. The system as claimed in claim 1, wherein the means for reducing motion of the patient's cheeks comprises a nozzle fixed to the initial end of the cavity, the nozzle comprising a cheek supporting system comprising two plates positioned laterally to a mouthpiece and configured to be positioned external to the patient's cheeks.

8. The system of claim 1, wherein the rotational velocity of the motor is varied such as to force external air into the cavity to produce the pressure variations.

9. A method for measuring the mechanical impedance of a patient's respiratory system during a spontaneous breath, comprising the step of recording air pressure and air flow measurements of the patient; said recording step comprising stages of varying the rotational speed of a fan positioned within a cavity for controlling a pressure within the cavity such as to force an air flow into said cavity to generate, in proximity to an airway opening of said cavity, pressure oscillations of maximum amplitude less than or equal to 3 $cmH_2O$ and frequencies greater than 2 Hz; enabling said patient to breathe spontaneously through said cavity, containing said fan; said cavity having a maximum impedance equal to 1 cm $H_2O/L/s$, measured at normal breathing frequencies within the range of 0-1 Hz; and measuring the air pressure and air flow within said cavity in proximity to the patient's airways.

10. The method of claim 9, further including the step of supporting the patient's cheeks.

11. The method of claim 9, further including the step of providing a nozzle fixed to an initial end of the cavity, the nozzle comprising a cheek supporting system having two plates positioned laterally to a mouthpiece and configured to be positioned external to the patient's cheeks.

12. The method of claim 9, further including the step of controlling a rotational velocity of a motor associated with the fan to force external air into the cavity to produce the pressure oscillations.

13. A portable system for self-assessment of the mechanical impedance of a patient's respiratory system during a spontaneous breath, comprising a fan; a motor which operates said fan; said motor and said fan being positioned within a cavity and a speed of the fan controlling a pressure within the cavity; said cavity comprising an initial end and a final end, both providing access to an outside of the cavity; said cavity having a length between said initial end and said final end equal to or less than 25 cm; said cavity, including said motor and said fan, comprising an impedance between said initial end and said final end of less than 1 cm $H_2O/L/s$, measured at normal breathing frequencies within the range of 0-1 Hz; said fan having a total area not exceeding three-fourths of the area of a cross-section of the cavity; said fan withdrawing air from said final end and providing pressure variations, with maximum peak-peak amplitude equal to or less than 3 $cmH_2O$ and frequency greater than 2 Hz, to said initial end; said initial end comprising an air pressure and an air flow measurement sensor and a connection configured to be directly connected to an airway opening of the patient, and including a nozzle adapted for reducing the motion of the patient's cheeks.

14. The system of claim 13, wherein the nozzle includes two plates positioned laterally to a mouthpiece, the plates being configured to be positioned external to the patient's cheeks.

15. The system of claim 13, wherein a rotational velocity of the motor is varied such as to force external air into the cavity to produce the pressure variations.

* * * * *